United States Patent [19]
Alpern et al.

[11] Patent Number: 5,356,006
[45] Date of Patent: Oct. 18, 1994

[54] STERILE PACKAGE FOR SURGICAL DEVICES

[75] Inventors: Marvin Alpern, Glen Ridge, N.J.;
Robert Cerwin, Pippersville, Pa.;
Michael O'Toole, Suffern, N.Y.;
Teresa M. Simons, Milltown;
Deborah M. Transue, Bridgewater, both of N.J.

[73] Assignee: Ethicon, Inc., Somerville, N.J.

[21] Appl. No.: 991,602

[22] Filed: Dec. 16, 1992

[51] Int. Cl.⁵ ............................................. B65D 83/10
[52] U.S. Cl. ..................................... 206/363; 206/364; 206/438; 206/523
[58] Field of Search ............... 206/363, 364, 438, 439, 206/523

[56] References Cited

U.S. PATENT DOCUMENTS

| | | | |
|---|---|---|---|
| 3,520,401 | 7/1970 | Richter et al. | 206/438 |
| 3,802,555 | 4/1974 | Grasty et al. | 206/438 |
| 4,057,144 | 11/1977 | Schuster | 206/439 |
| 4,173,219 | 11/1979 | Lentine | 604/77 |
| 4,300,543 | 11/1981 | Rhee . | |
| 4,523,679 | 6/1985 | Paikoff et al. | 206/363 |
| 4,524,868 | 6/1985 | Buckley et al. | 206/364 |
| 4,730,729 | 3/1988 | Monch | 206/363 |
| 4,750,619 | 6/1988 | Cohen et al. | 206/438 |
| 4,798,292 | 1/1989 | Hauze | 206/363 |
| 5,072,832 | 12/1991 | Valentine et al. | 206/438 |
| 5,084,005 | 1/1992 | Kachigian | 604/1 |
| 5,176,258 | 1/1993 | Antal | 206/438 |

Primary Examiner—David T. Fidei
Attorney, Agent, or Firm—Paul A. Coletti

[57] ABSTRACT

A sterile package for endoscopic devices. The package includes a foam member that holds the endoscopic device in a stable position within the package. The package includes at least one sterile overwrap member and one non-sterile overwrap member.

15 Claims, 8 Drawing Sheets

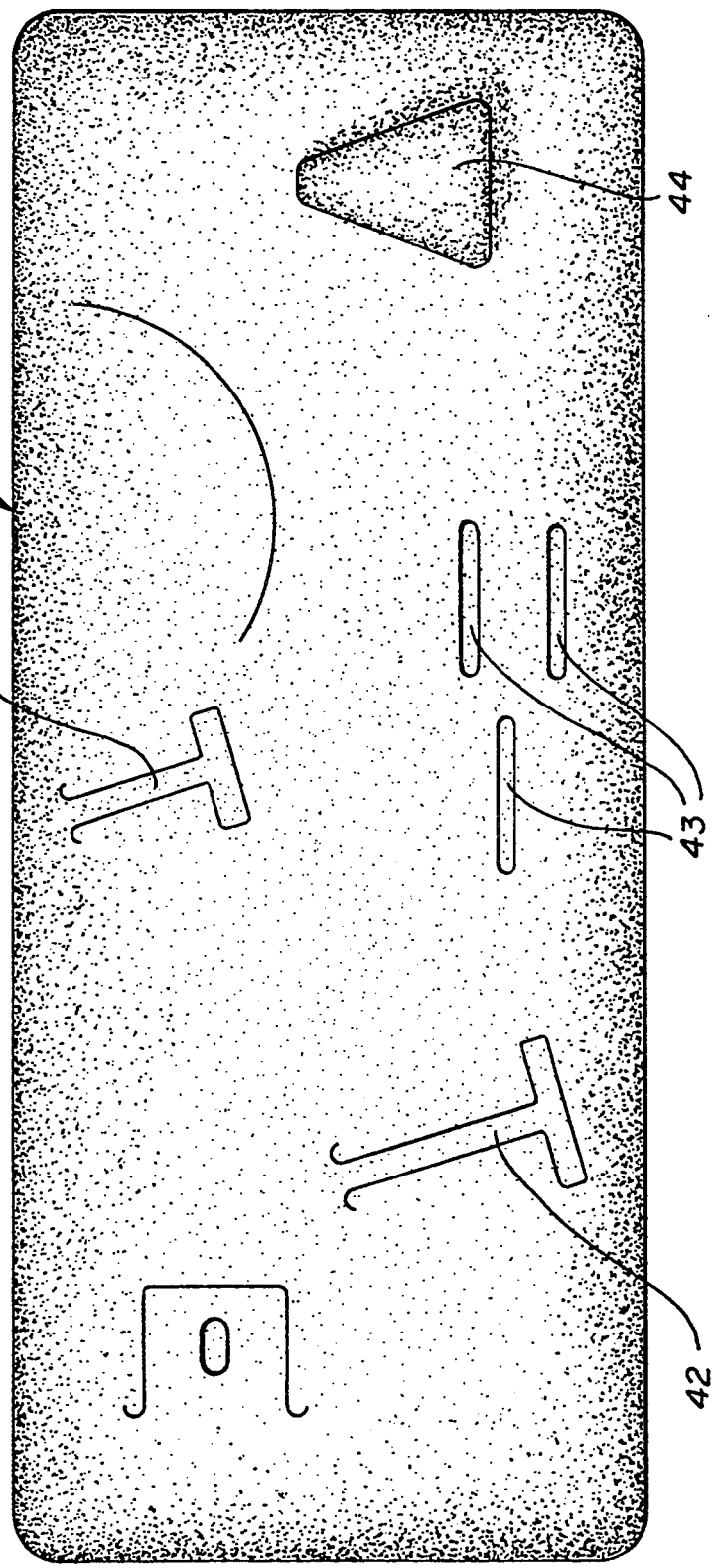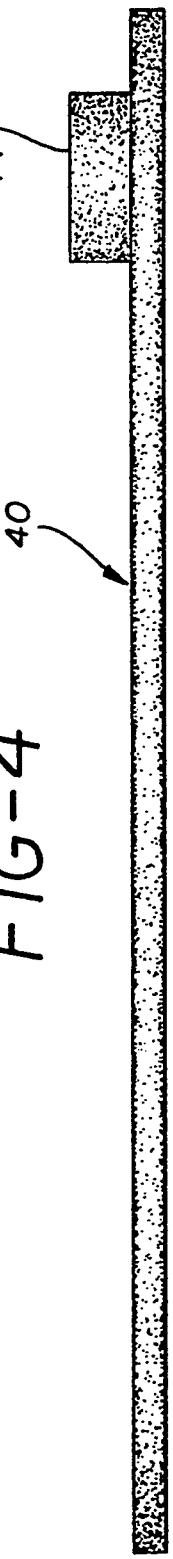

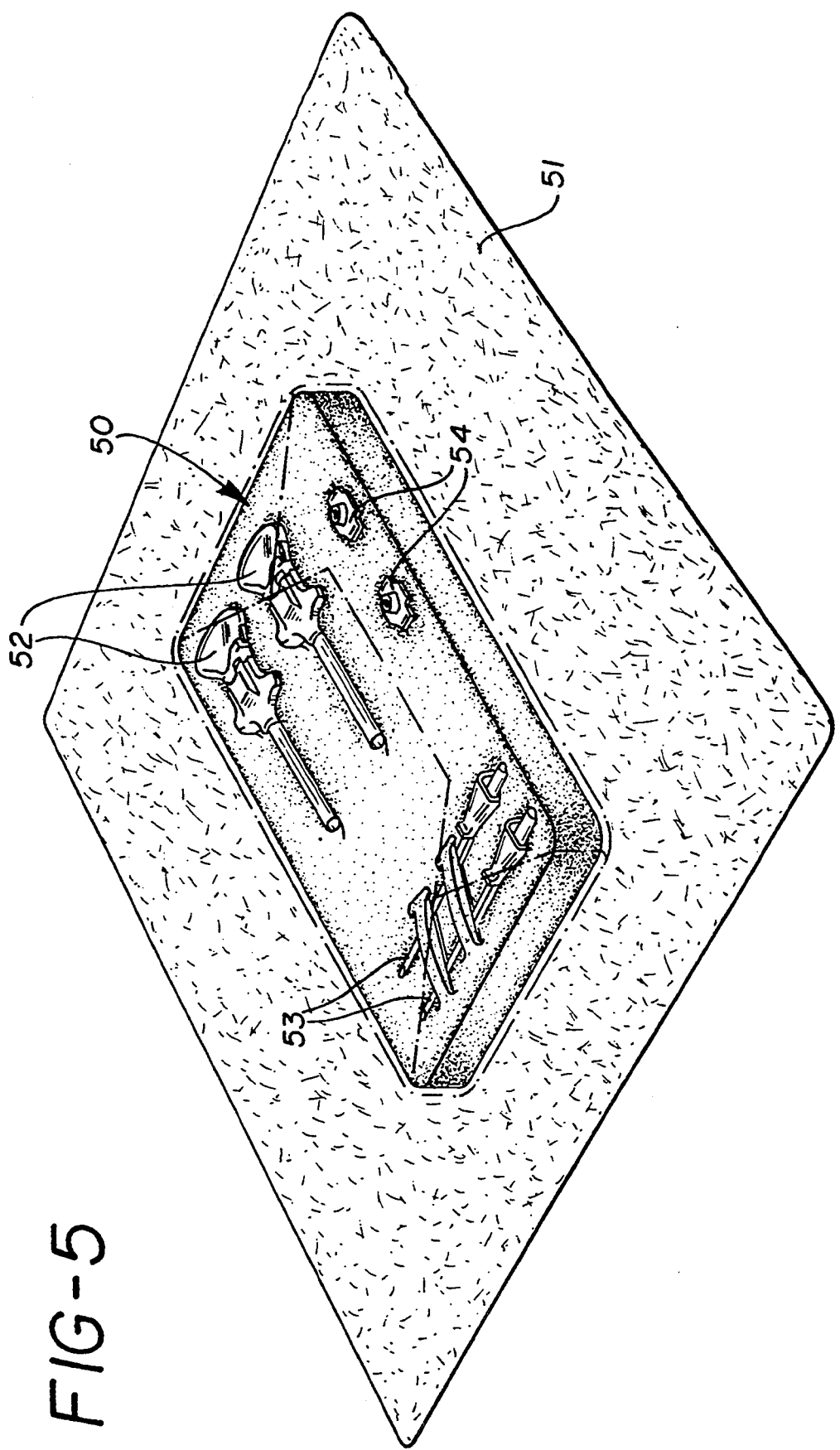

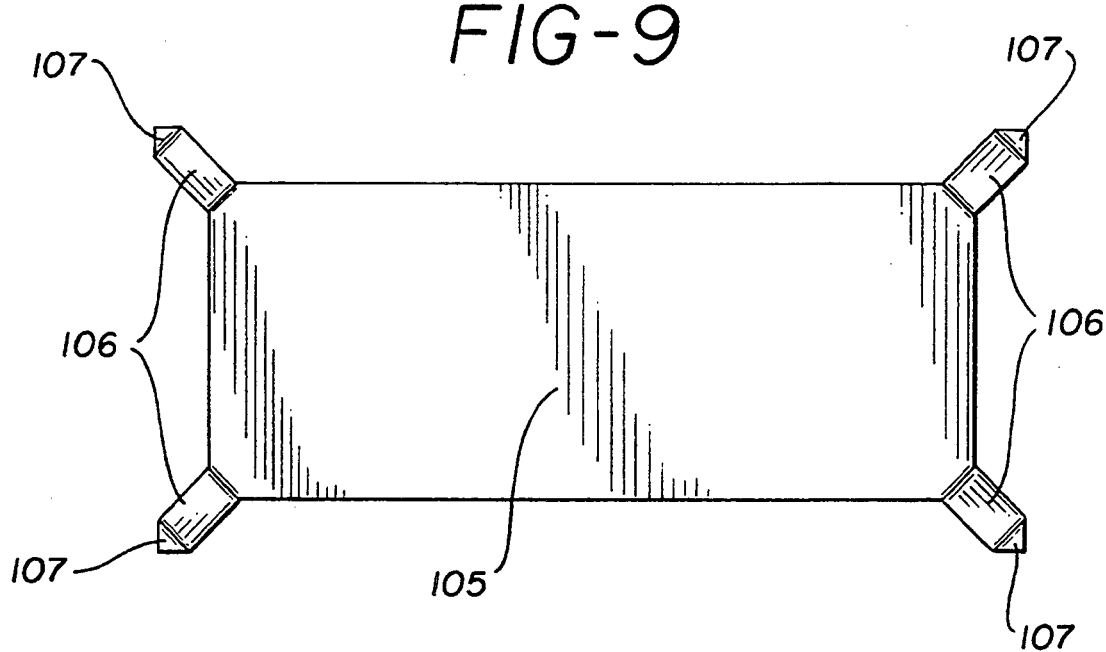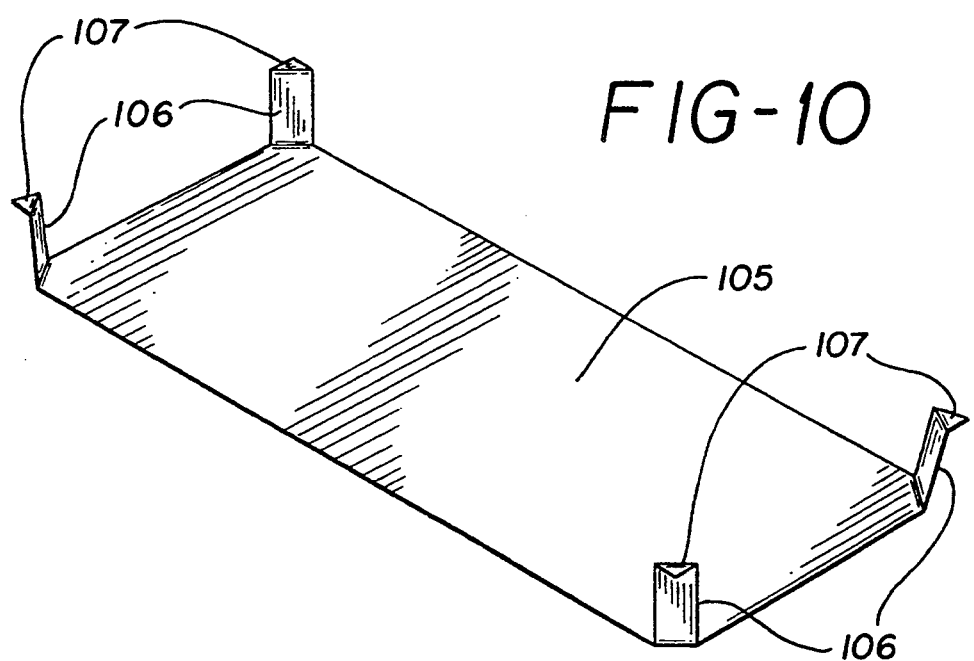

STERILE PACKAGE FOR SURGICAL DEVICES

FIELD OF THE INVENTION

This invention relates to a sterile package for surgical devices which are to be used in surgical procedures. More specifically, this invention relates to a sterile package which may be readily placed in a sterile field and reduces the problems associated with the disposal of such package.

BACKGROUND OF THE INVENTION

Endoscopic surgery has been gaining wide acceptance as an improved and cost-effective technique for conducting certain surgical procedures. In these procedures, various endoscopic devices are used; such as, trocars, Veress needles, clip appliers, stapling instruments, forceps, scissors, etc. The devices, and especially certain of the surgical instruments, are quite heavy and cause considerable packaging problems. This is also true for the devices and instruments used in standard surgery or open surgery. The package must insure that the instrument is maintained sterile during transportation and storage and remains that way until used. The package should be such as to make the instruments readily accessible and in a sterile condition when presented to the sterile operating site. This has required, in many instances, the use of thermo-formed plastic packages to hold the instruments. Often, a package will include a number of surgical devices. The package may include all the devices to be used in one specific endoscopic procedure. For example, a package may incorporate two or three trocars, various adapters for the trocars, obturators, sleeves, a Veress needle, forceps, scissors, a multiple clip applier and a stapling or fastening instrument. These packages become quite bulky and cumbersome to handle, and require that a non-sterile or circulating nurse open the package and then a sterile or operating room nurse remove the sterile contents.

Also, as can be appreciated, disposing of materials in hospitals, especially materials used in the operating room presents considerable problems to hospitals. In fact, certain materials, such as those used in the operating theaters, must be disposed of in what is termed "red bag" disposable. This requires that extra caution and care be used in disposing of such material which causes added expense for the hospital. Also, it is extremely important that materials disposed of in such a manner do not puncture the containers used for disposal. The thermo-formed packages, especially those containing a plurality of instruments or devices have caused hospitals considerable disposal problems.

It is an object of the present invention to provide a package which is readily presentable in the sterile environment with a minimum of effort. It is an object of the present invention to provide a package that can be easily handled and reduces disposal problems. It is a further object of the present invention to provide packages which require less volume and, hence, less storage area and maintain the devices in a stable state throughout transportation and storage.

SUMMARY OF THE INVENTION

Briefly, the present invention comprises a sterile package in which a surgical instrument is positioned on a foam member, preferably a closed cell foam member, with the foam member conforming to a portion of the surface of the instrument to stabilize the instrument within the package. More specifically, the present invention comprises a sterile package for endoscopic devices. The package includes a foam member, most preferably a closed cell foam member and more than one such foam member. Positioned on the foam members are the endoscopic devices and instruments to be used in an endoscopic procedure. Preferably, the foam members with the devices thereon are held in a substantially rectangular, relatively rigid member. The rigid member is encased in a series of overwraps. The innermost overwrap is a sterile overwrap and totally encloses the rigid member and the foam members. The outer most wrap is non-sterile and totally encloses the entire package. The outer wrap includes a portion that is readily removable from the outer wrap to provide ready and easy access to the sterile materials inside.

BRIEF DESCRIPTION OF THE DRAWINGS

FIG. 3 is a top view of a closed cell foam member;

FIG. 4 is a side view of the closed cell foam member shown in FIG. 3;

FIG. 5 is a perspective view of a sterile overwrap with a closed cell foam member and endoscopic devices thereon.

FIG. 9 is a perspective view of an insert that may be used with the relatively rigid member depicted in FIG. 7; and FIG. 10 is a plan view of the insert depicted in FIG. 9.

DETAILED DESCRIPTION OF THE DRAWINGS

Figure 1:
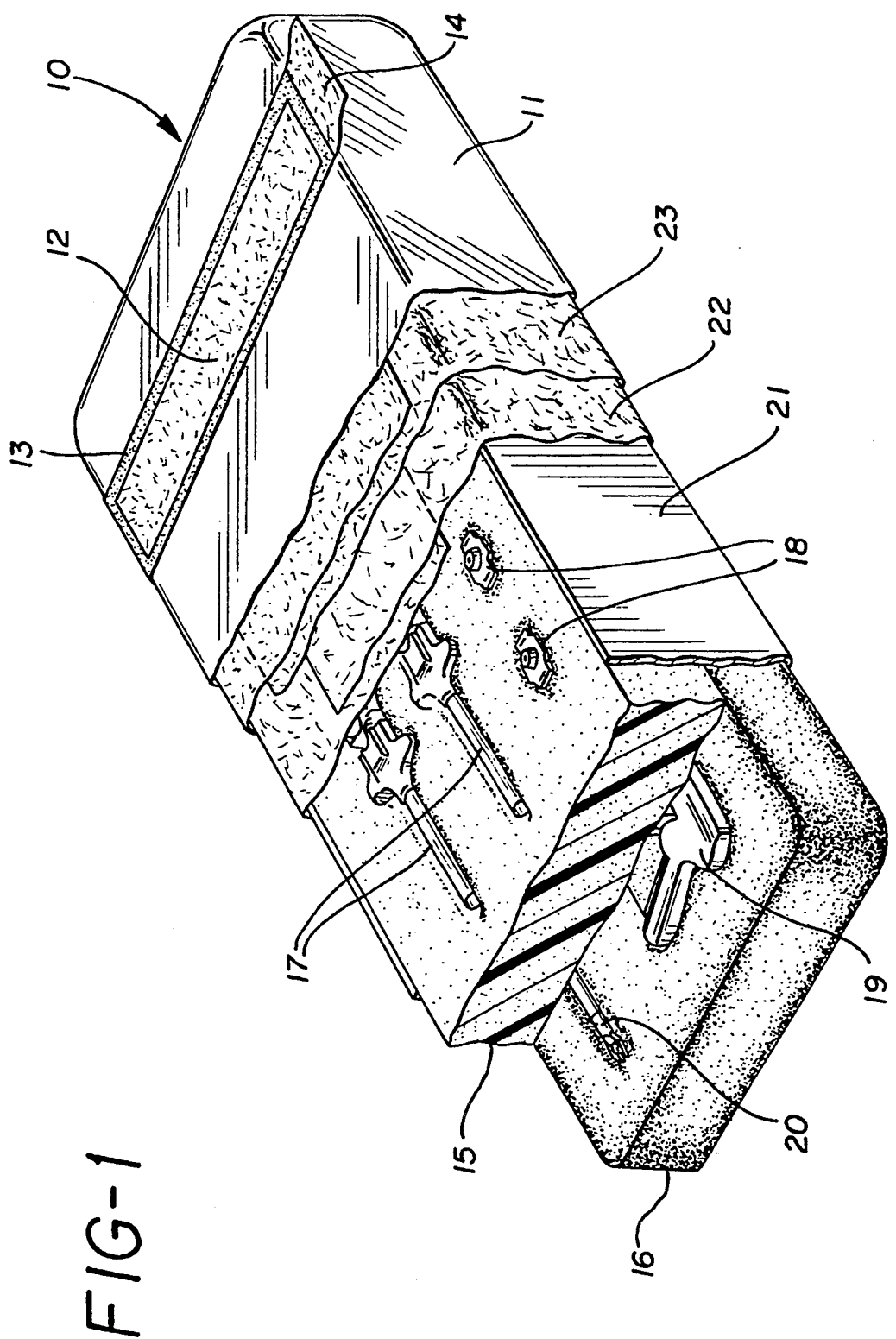
FIG. 1 is a cut-away perspective view of a sterile package of the present invention showing the various individual items within the package.

Referring to the drawings, FIG. 1 is a perspective view of a sterile package 10 for endoscopic devices in accordance with the present invention. The view is a partial cut away view to show the various members within the sterile package. The package comprises an outer wrap 11; for example, a polyethylene bag. While a polyethylene bag is preferred, the outerwrap can be made of nonwoven fabric materials or other plastic materials. At one end of the bag there is a peel strip 12. This is a strip of material; such as a nonwoven fabric, which has been heat sealed 13 about its periphery to the polyethylene bag. A portion 14 of the strip overlaps the end of the bag to provide an area that can be readily grasped by the user to tear off the peel strip and expose the contents of the bag. Disposed inside the bag are two or more trays or layers 15 and 16 of closed cell foam material. Disposed on each closed cell foam layer are the various instruments and devices to be used in a surgical procedure. On the upper layer there are trocars 17 and adapters for trocars 18 and on the bottom layer there is a stapling instrument 19 and a clip applier 20. The layers are encased in a box 21, though the top of the box is not shown in order to show the layers and instruments for the sake of clarity. The box has a floor and four lateral side walls and the layers fit snugly within that box.

The box with the foam layers inside are encased in a first overwrap 22. This overwrap may be made from nonwoven fabric materials and is a sterile overwrap. There is also a second sterile overwrap 23 which encases the first sterile overwrap. It is preferred that the second sterile overwrap be folded in such a manner that it may readily be grasped through the peel strip opening in the outer bag. Surgical drape materials as are well known in the art may be used for the sterile overwraps. It is preferred that the inner or first sterile overwrap be sufficiently large to cover the "Mayo" stand or other stand being used in the operating room. In use, the bag may be easily opened by the circulating nurse. The circulating nurse would peel back the strip. Once the strip is removed, the nurse may grab the outer sterile overwrap by the appropriate corner and pull out the entire contents from the bag. The outer overwrap may then be unfolded without touching the inner sterile overwrap, leaving a sterile package in the sterile environment ready for use by the operating room personnel. The operating room personnel need only touch the inner sterile overwrap in order to access the sterile instruments inside. This eliminates the need for two people being available simultaneously in order to open the bag. With our new package the circulating nurse may open the package whenever most convenient for the nurse. The operating room personnel may also open the sterile instruments at a time most convenient for them. Also, the operating room personnel may use the inner sterile overwrap as the "Mayo" stand cover.

Figure 2:
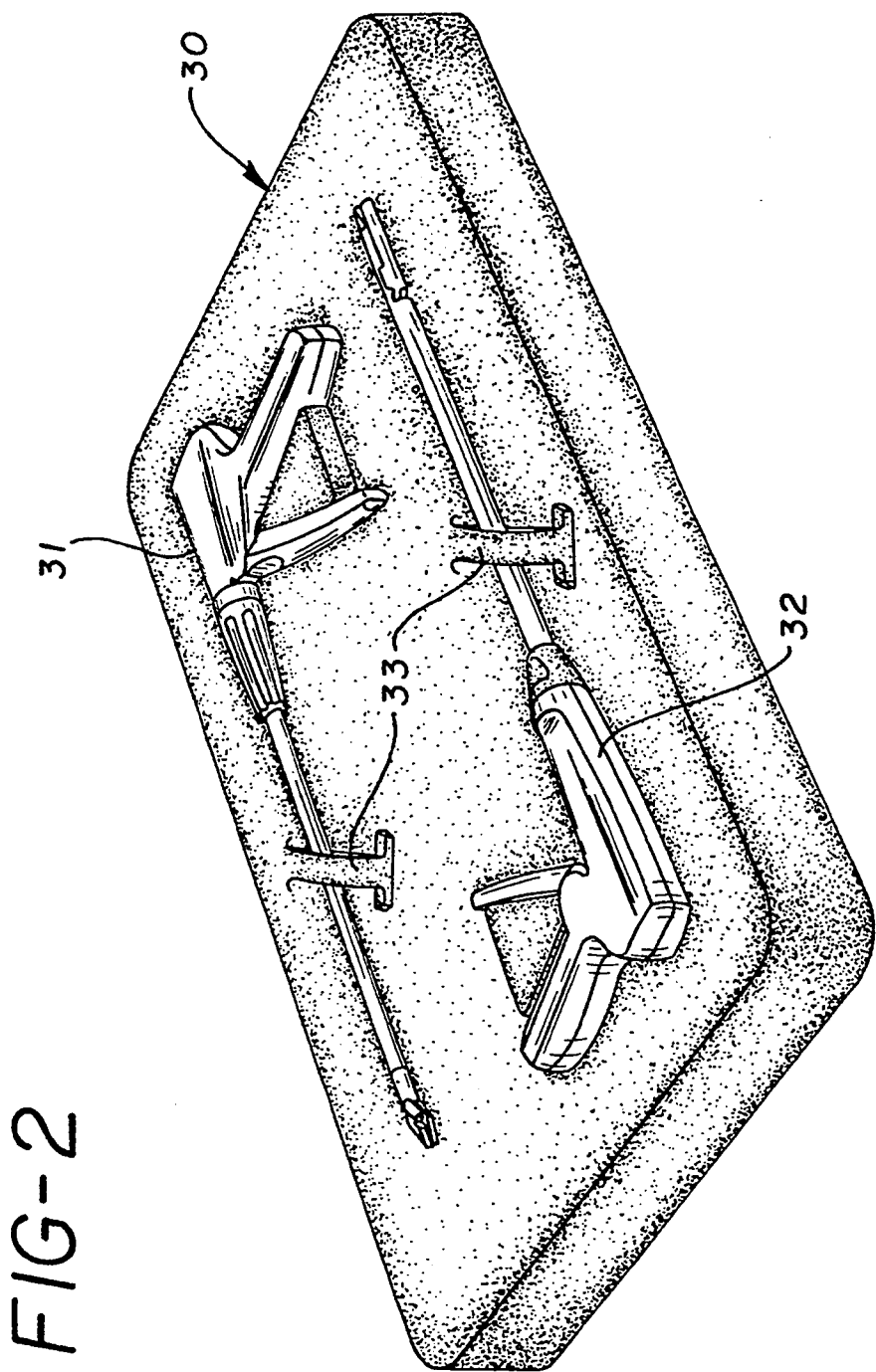
FIG. 2 is a perspective view of a closed cell foam member used in the sterile package of the present invention.

Referring to FIG. 2 there is shown a perspective view of a closed cell foam member 30 used in the package of the present invention. The closed cell foam member is die cut with rounded corners to reduce the possibilities of punctures or tearing of the overwraps. In this embodiment, the instruments are multiple clip applier 31 and a stapling instrument 32. Both instruments are held in place on the foam by a piece 33 which has been die cut from the foam. The piece has one end attached to the foam with the other end placed over a portion of the instrument and then back into the foam to aid in holding the instrument in place on the foam. The closed cell foam should have a density of from about 2 to 6 pounds per cubic foot and a cell size of from 30 cells per sq. in. to 500 cells per sq. in. Preferably, the cell size will be from about 150 to 350 cells per sq. in. Closed cell foams of various polymers such as the polyurethanes, the polyethylenes, the polyesters, the polyethers and the like may be used. The closed cell foam will take a set from the weight or the pressure of the instruments placed on its surface and will conform to the outside configuration of the instrument to assist in holding the instrument in place. A specific closed cell foam suitable for use in the present invention is a mini-cell blown high density polyethylene closed cell foam having a density of 2 pounds per cubic foot and approximately 300 cells per square inch.

Closed cell foams provide great flexibility in the manufacture of the foam cell members in that they can be cut in any pattern or configuration depending upon the devices to be packaged for a specific surgical procedure. On placing the instrument on the closed cell foam the slight pressure forces the air from the foam and allows the foam to deform itself around the instruments. Another advantage to the closed cell foam is that it doesn't develop a particulate material when die cut or otherwise manipulated as do many other materials. This is extremely important in the packaging of surgical instruments as particulate material is very undesirable within the surgical environment. Also, the closed cell foam is easier to sterilize because there are few cracks, nooks and crannies in the foam material and if the package must be sterilized by ethylene oxide it is easier for the gas to get to all of the surfaces of the foam material and provide sterilization. It should be pointed out that the packages of the present invention may be sterilized by any of the known techniques such as ethylene oxide, cobalt sterilization, etc. The sterilization technique used will be determined by the materials used in the instruments and whether those materials are readily sterilized by irradiation, ethylene oxide etc. Also, the closed cell foam materials may be glued or printed as desired. Furthermore, certain of the closed cell foam materials may be thermoformed or skived (i.e., cut or sliced into layers or pieces to aid in conforming the foam to the devices or to other foam layers. The closed cell foams are easier to slit or cut than the open cell foams and are also more rigid which is especially desirable with the heavier, bulkier types of endoscopic instruments presently being developed. Closed cell foam materials may be injection molded into desired shapes and configurations and used in the packages of the present invention.

A preferred closed cell foam member useful in the package of the present invention is shown in FIGS. 3 and 4. FIG. 3 is a plan view of the member 40 and FIG. 4 is a side view of the member. As may be seen in FIG. 3, T-shaped crosses 41 and 42 are die cut in the closed cell foam member. The base of the T remains attached to the member while the remainder of the T may be lifted from the foam member. It is a simple matter when placing the instruments on the foam member to place the T over the instrument and insert the cross of the T back into the cut-out space to aid in holding the instruments in place. Also, various pockets 43 may be die cut in the closed cell foam member to provide holding areas for various devices used in endoscopic surgical procedures. As many of the instruments have trigger handles and it is desirable to hold that handle in a given position, it is a simple matter to take a second piece 44 of closed cell foam and glue it to the first layer so that the trigger portion of an instrument may be appropriately placed over that additional closed cell foam portion to hold a trigger in a given position during transportation and storage of the package.

As previously mentioned, the closed cell foam members are preferably encased in a box. It is preferred that the box be relatively rigid and to be opened at the top. The box may be made of Kraft sulfite board or similar materials. The box performs a number of functions in that it is used to hold the closed cell foam members in place. It may also be used to stack the various instruments to provide ready access to the instruments during the surgical procedure. Furthermore, the box may be used as a disposal mechanism in that all the instruments after use may be placed in the box for disposal. Many of the instruments have either sharp edges or sharp points which could puncture the materials in which they are being disposed; hence, by placing the instruments in the box you eliminate this problem of puncturing.

In a preferred embodiment of the present invention, the foam members with the devices and instruments positioned thereon are held in a specially designed box as will be described in conjunction with FIGS. 7 through 10. The box is a relatively rigid member designed so that it will not puncture or abrade the overwraps and can be used as a container for the "red-bag" disposal of the devices, instruments and other material used in the surgical procedure.

Figure 7:
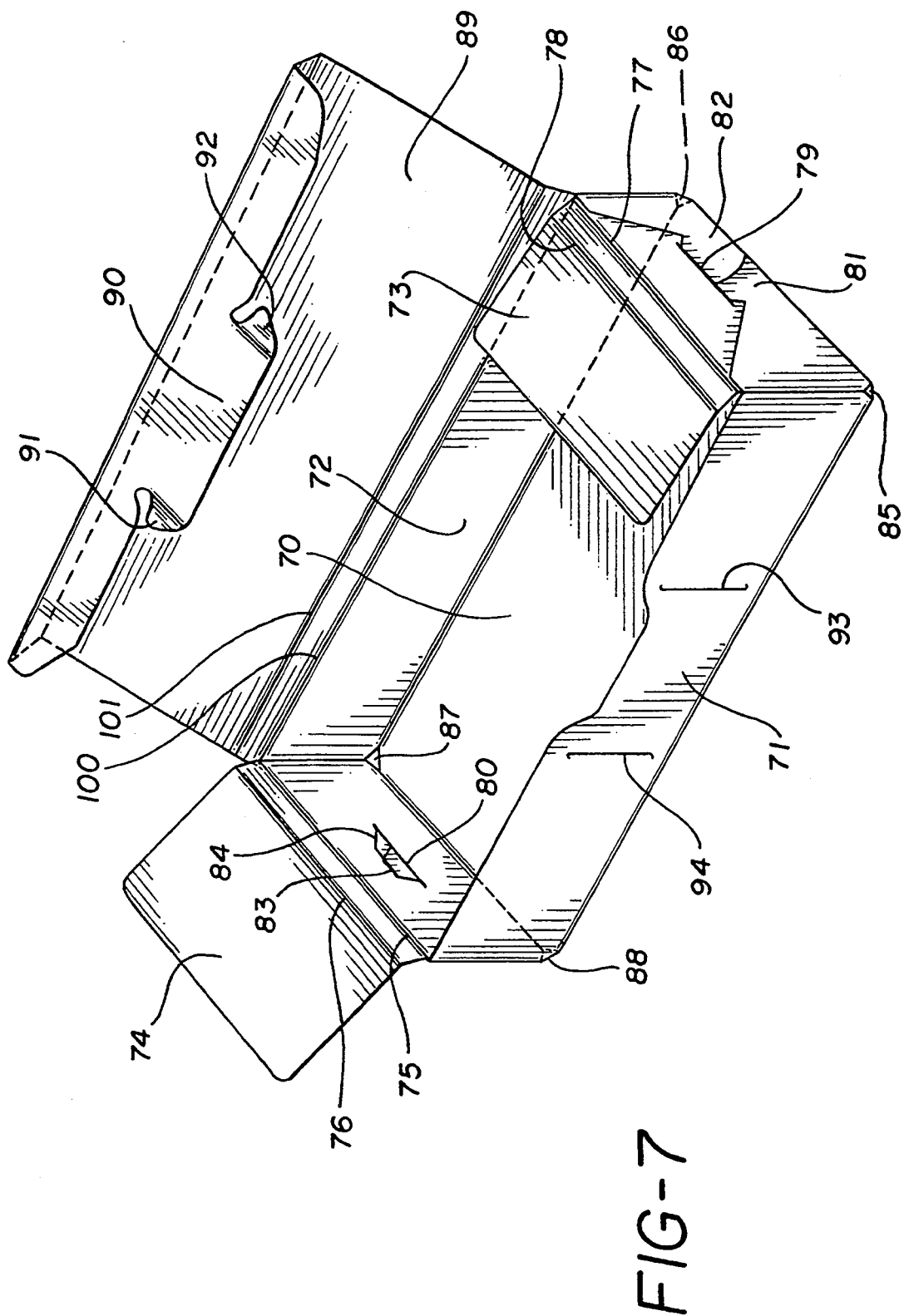
FIG. 7 is a perspective view of a relatively rigid member for use in the package of the present invention.
Figure 8:
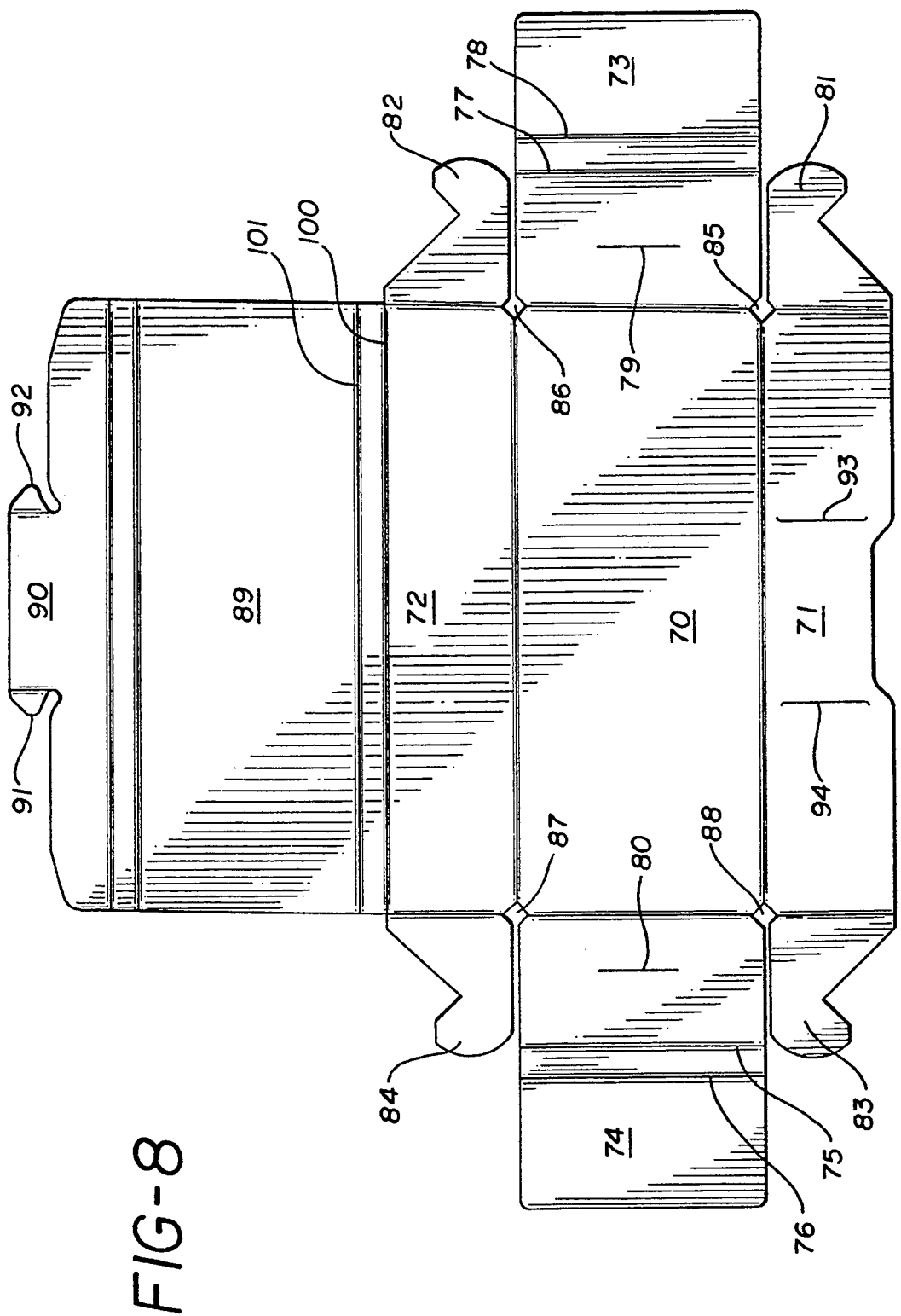
FIG. 8 is a plan view of the rigid member depicted in FIG. 7.

Referring to FIGS. 7 and 8, the box comprises a bottom 70, preferably rectangular in shape. A pair of longitudinal side walls 71 and 72 are attached to the longitudinal edges of the bottom, and a pair of transverse side walls 73 and 74 are attached to the transverse edges of the bottom. The transverse side walls include fold lines 75, 76, 77 and 78 to allow the upper half of the transverse side wall to be folded inwardly. The bottom portion of each transverse side wall has a slot 79 and 80 therein. At each end of both longitudinal side walls there is attached a foldable flap 81, 82, 83 and 84 so that when all four side walls are folded upwardly, the flaps may be inserted into the slits in the transverse side walls and provide stability to the box. At each of the four corners of the bottom, there is a diamond shape cutout area 85, 86, 87, and 88. These areas provide rounded corners when the box is formed. Attached to one longitudinal side wall at the edge of the wall opposite the edge attached to the bottom is the top 89 of the box. The top may be folded along either of the fold lines 100 or 101. A foldable flap 90 is attached to the top so that on folding the flap will contact the opposite longitudinal side wall. The flap includes a pair of extending tabs 91 and 92 which may be inserted into slits 93 and 94 disposed in the opposite longitudinal side wall to provide further rigidity to the box. It is desirable to use flaps or tabs inserted into slits to provide stability in the box rather than glue or adhesive. Glues and adhesives may cause both sterility and environmental problems. It is preferred that a plurality of fold lines be used wherever appropriate to allow for varying heights of boxes to be produced from a single cutout blank.

In order to use the box described above for the disposal of instruments, devices and the like after being used in the operating room, it is important that the openings forming the founded corners be closed. This is accomplished by using an insert in the box. Such an insert is depicted in FIGS. 9 and 10. The insert comprise a bottom member 105 sized to cover the inside of the floor or bottom of the box. At each corner of the bottom member is a vertical member 106 which is attached diagonally at each corner.

Extending outwardly from the top of each vertical member is a horizontal member 107 having a triangular shape. When this insert is placed in the box, the vertical members will cover the corner holes formed by the diamond cutouts with the triangular shaped horizontal members abutting a longitudinal and transverse sided wall. The construction described allows the operating personnel to place items after use into the box. After the procedure is complete, the box may be closed and easily and readily sent for disposal.

Referring to FIG. 5, there is shown a closed cell foam member 50 used in the package of the present invention placed on a first sterile overwrap 51. The closed cell foam member has trocars 52, Veress needles 53 and various trocar adapters 54 disposed on the member. The dotted lines indicate the folding of the sterile overwrap over the closed cell foam member to totally encase the member and the devices. If desired, sterile towels or sterile wipes may be included in the package along with the endoscopic devices.

Figure 6:
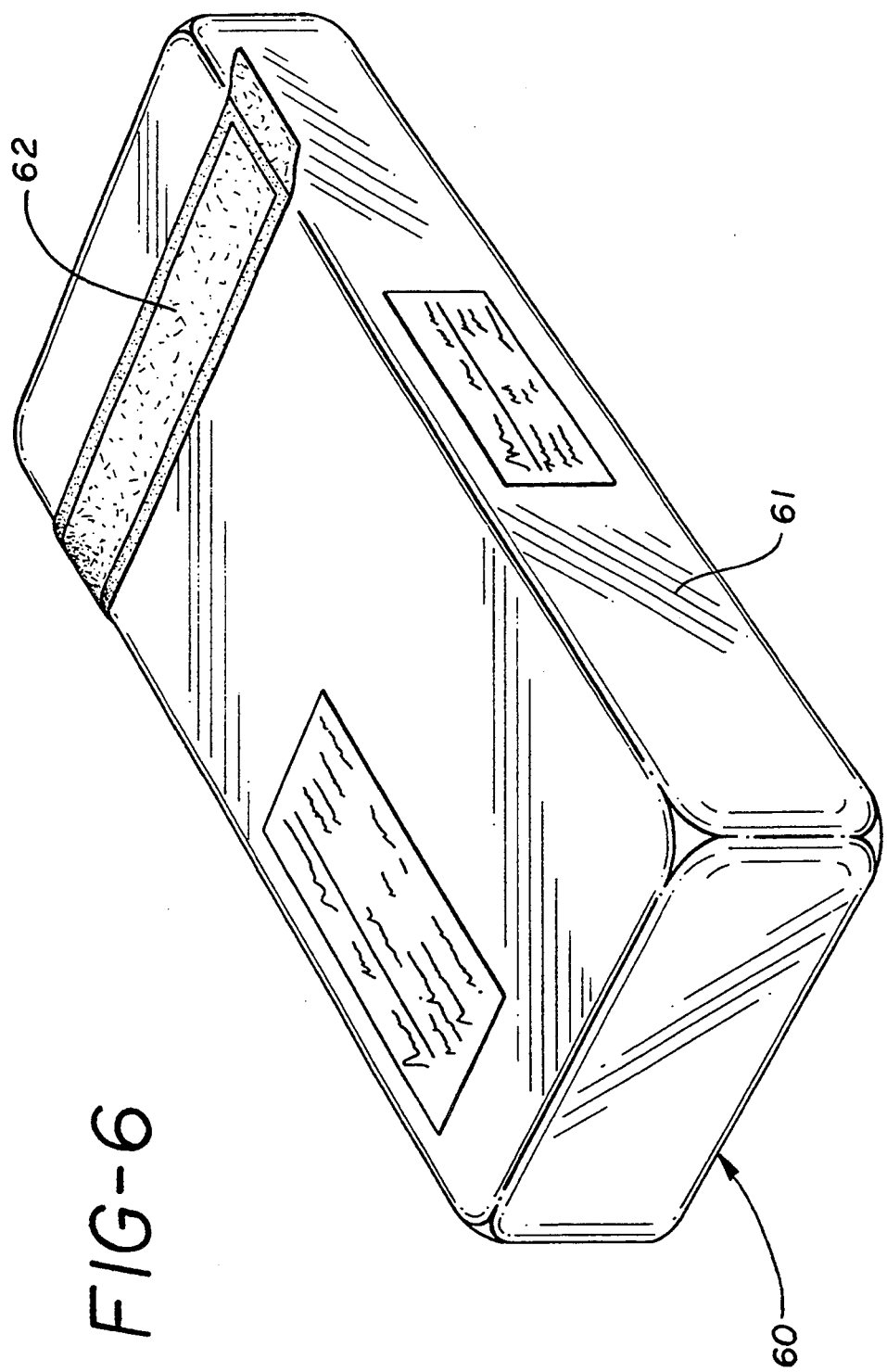
FIG. 6 is a perspective view of a sterile package in accordance with the present invention.

FIG. 6 is a perspective view of a sterile package of the present invention. The package 60 is a clear polyethylene bag 61. The bag includes a heat sealed peel strip 62 over a portion of its surface. The contents of the bag are as previously described in conjunction with FIG. 1. As may be seen, a label or other printed material may be incorporated within the bag to inform the user of the contents of the bag or other useful information.

An advantage to the package of the present invention, especially as compared to the prior art, thermoformed plastic members, is the stability of the devices during transportation and in handling. Often, thermo formed plastic packages may crack or be otherwise compromised from the heavy instruments packaged therein. This is especially true if the package is roughly handled during transportation. This problem is overcome with the packages of the present invention. Another problem of the thermo formed package is that in order to hold the instrument in a stabilized position within the package, it is common practice to form undercuts in the thermo-formed member package and place the instrument with force into those undercut areas to hold the instrument stable. This often causes the operating room personnel difficulty when they try to remove the instruments from the thermo-formed package.

As previously mentioned, a considerable concern to hospital personnel is the disposal of materials used in a hospital. This is especially true of materials used in operating rooms. In fact, certain materials used in the hospital must be disposed in what is termed "red bag disposal". These are materials which have been used in the operating room or in highly infectious areas, etc. Disposal in the "red bag" area is costly and it is desirable for the hospital to keep the amount of such disposal to a minimum. The packages of the present invention assist in this regard in that the outer wrap need never enter the operating room and, hence, will not require red bag disposal. One or even both of the sterile wraps may be removed outside the operating room and the sterile nurse take the closed cell foam members into the operating room. This would mean that the overwraps would not have to be disposed in red bag disposal.

Furthermore, the package may be made of substantially clean burning materials; that is, materials whose combination products are carbon dioxide and water. This is another advantage for the hospitals to assist them in the disposal of packaging materials. Examples of suitable materials are polyethylene terephthalate, polyethylene, polyproplene and the like.

Although the invention has been described by way of a specific example and of preferred embodiments thereof, it will be evident that other adaptations and modifications may be employed without departing from the spirit and scope of the present invention.

What is claimed is:

1. A sterile package for a surgical instrument, said package comprising:
   a closed cell foam member, said foam member having a density of from 2 pounds per cubic foot to 6 pounds per cubic foot
   at least one surgical instrument disposed on and held in position by said foam member,
   at least one sterile overwrap member enclosing said foam member and said instrument, and
   a second non-sterile overwrap member enclosing said sterile overwrap member.

2. A sterile package for a surgical instrument, said package comprising:
   a closed cell foam member, said foam member having a density of from 2 pounds per cubic foot to 6 pounds per cubic foot
   at least one surgical instrument disposed on and held in position by said foam member,
   at least one sterile overwrap member enclosing said foam member and said instrument,
   a second non-sterile overwrap member enclosing said sterile overwrap member, and
   wherein the closed cell foam member has a cell size of from 150 to 350 cells per square inch.

3. A sterile package according to claim 2 wherein said second non-sterile overwrap member includes a peelable portion providing for ready access to said sterile overwrap member.

4. A sterile package according to claim 2 wherein the non sterile overwrap member is a clear polyethylene bag member.

5. A sterile package according to claim 2 which includes a second sterile overwrap member enclosing said one sterile overwrap member.

6. A sterile package for surgical devices, said package comprising;
   at least two foam members,
   at least two endoscopic devices, one of said devices being disposed on one of said foam members and the other of said devices being disposed on the other of said foam members,
   a substantially rectangular, relatively rigid member having a floor and four lateral walls extending vertically from said floor,
   said foam members and said devices being disposed within said relatively said rigid member,
   a first sterile overwrap member enclosing said relatively rigid member,
   a second sterile overwrap member enclosing said first sterile overwrap member; and
   non-sterile outerwrap enclosing said second sterile overwrap member, said outerwrap including a portion that is removable from said outerwrap to provide ready access to said second sterile overwrap member.

7. A sterile package according to claim 6 wherein the non-sterile outerwrap member includes a portion that is removable from said outerwrap to provide ready access to said second sterile overwrap member.

8. A sterile package according to claim 6 wherein the closed cell foam members have a foam density of from 2 pounds per cubic foot to 6 pounds per cubic foot.

9. A sterile package according to claim 6 wherein the foam members are closed cell foams.

10. A sterile package according to claim 9 wherein the closed cell foam have a density of from about 2 pounds per cubic foot to 6 pounds per cubic foot.

11. A sterile package according to claim 10 wherein the closed cell foams have a foam cell size of from about 150 to 350 cells per square inch.

12. A sterile package according to claim 6 wherein the substantially rectangular relatively rigid member is made of Kraft sulfite paper board.

13. A sterile package according to claim 6 wherein the non-sterile outerwrap is a clear polyethylene bag.

14. A sterile package according to claim 6 wherein the substantially rectangular or rigid member includes a top member to form an enclosed box.

15. A sterile package according to claim 7 wherein the foam members are the foam members having a density of from 2 pounds per cubic foot to 6 pounds per cubic foot, said substantially rectangular or rigid member includes a top member to form an enclosed box, said non-sterile outerwrap is a clear polyethylene bag, which includes a portion that is removable from said outerwrap to provide ready access to said second sterile overwrap member.

* * * * *